United States Patent [19]

Devos et al.

[11] 4,288,619

[45] Sep. 8, 1981

[54] PROCESS FOR THE RECOVERY OF α-HYDROXY- AND α-AMINO-CARBOXYLIC ACIDS FROM SUGAR-CONTAINING MEDIA

[75] Inventors: Francis Devos; Michel Huchette, both of Lestrem, France

[73] Assignee: Roquette Freres, France

[21] Appl. No.: 71,371

[22] Filed: Aug. 30, 1979

[30] Foreign Application Priority Data

Aug. 31, 1978 [FR] France .............................. 78 25239

[51] Int. Cl.$^3$ ...................... C07C 51/00; C07C 51/42; C07C 99/00
[52] U.S. Cl. .................................... 562/554; 562/515; 562/580; 127/46 A; 210/198.2
[58] Field of Search ............. 210/38 A, 692; 562/515, 562/554, 573, 589, 580; 127/46 A

[56] References Cited

U.S. PATENT DOCUMENTS

| | | | |
|---|---|---|---|
| 2,738,367 | 3/1956 | Redmore | 562/515 |
| 2,949,450 | 8/1960 | Stark | 562/573 |
| 3,015,655 | 1/1962 | Stark | 562/554 |
| 3,505,399 | 4/1970 | Samejima et al. | 562/554 |

OTHER PUBLICATIONS

Kirk–Othmer *Encyclopedia of Chemical Technology*, vol. 11, pp. 871–880, (1963) Interscience Publ., 2nd Ed.

*Primary Examiner*—Natalie Trousof
*Assistant Examiner*—L. Hendriksen
*Attorney, Agent, or Firm*—Larson and Taylor

[57] ABSTRACT

The invention relates to a process for the recovery of α-hydroxy- and α-amino-carboxylic acids from sugary media containing them.

According to the process of the invention:
  in a first phase, the mixture from which it is proposed to recover the α-hydroxy- or α-amino-carboxylic acid and which contains the latter in the form of its calcium salt is contacted with a cationic resin in the calcium form for a sufficient time to reach optimal adsorption of said calcium salt and then,
  in a second phase, the previously saturated resin is eluted by resorting to water.

The process according to the invention enables the quantitative production of a pure calcium salt.

13 Claims, 7 Drawing Figures

U.S. Patent  Sep. 8, 1981  4,288,619

PROCESS FOR THE RECOVERY OF α-HYDROXY- AND α-AMINO-CARBOXYLIC ACIDS FROM SUGAR-CONTAINING MEDIA

The invention relates to a process for the recovery of α-hydroxy- and α-amino-carboxylic acids from sugar-containing media.

Various processes have been contemplated for recovering said acids from these mixtures.

Thus, it has been proposed to separate by crystallization from a mixture of oses, holosides or polyholosides constituting the raw material, the calcium salt of the desired aldonic acid and which has been prepared by specific biochemical oxidation.

The same technique by the crystallization route has been proposed for separating calcium lactate from the broth within which lactic acid has been generated by anaerobic fermentation.

Finally, it is used for recovering glutamic acid from broths based on carbohydrates from which this acid is prepared by fermentation.

These techniques do not give satisfaction both from the aspect of the recovery ratio of the calcium salt and from that of the purity of this salt, and it is a particular object of the invention to overcome this drawback and to provide a process and an installation adapted to obtain a quantitative recovery of a pure calcium salt.

To do this, conforming to the process according to the invention:

in a first phase, the mixture from which it is proposed to recover α-hydroxy- or α-amino-carboxylic acid and which contains the latter in the form of its calcium salt is contacted with a cationic resin in the calcium form for a sufficient time to reach optimal adsorption of said calcium salt and then, in a second phase, the previously saturated resin is eluted by resorting to the use of water.

According to an advantageous embodiment, the abovesaid process is applied to the recovery of calcium gluconate from sugary media which contain it and which have served for its preparation by specific biochemical oxidation.

According to another advantageous embodiment, the abovesaid process is applied to the recovery of calcium xylonate from sugary media containing it and which have served for its preparation by a specific biochemical oxidation.

According to yet another advantageous embodiment, the abovesaid process is applied to the recovery of calcium lactate from sugary media containing it and which have been used for its preparation by specific biochemical oxidation.

According to yet another advantageous embodiment, the abovesaid process is applied to the recovery of calcium glutamate from sugary manufacturing media containing it.

According to yet another advantageous embodiment, the abovesaid process is applied to the recovery of calcium aspartate from sugary media containing it.

The invention provides yet other features which are preferably used at the same time and which will be more explicitly considered below.

It will, in any case, be well understood by means of the additional description which follows and of the examples relating to preferred embodiments.

To carry out the complete recovery of α-hydroxy- and α-amino-carboxylic acids from sugary media containing them, first of all, in a first phase, the mixture which contains the acid in the form of its calcium salt is contacted with a cationic resin in the calcium form.

The resin utilized has a small particle size and low divinylbenzene cross-linking ratio.

In practice, a cationic resin of the sulphonated styrene-divinylbenzene type is used in calcium form of a granulometry comprised between 0.1 and 1 mm, preferably between 0.2 and 0.6 mm.

The cross-linking ratio is in practice comprised between 2 and 10%, preferably between 3 and 5%.

By way of example, it is indicated that the following resins identified by their tradename may be advantageously used:

| | |
|---|---|
| "CA 9220" | marketed by ROHM & HAAS |
| "LEWATIT TX W 40" | marketed by BAYER |
| "C 20" | marketed by the DIA-PROSIM company |

Advantageously, the above-defined resin is placed in thermostated columns.

The contact between the mixture to be treated and the resin must be sufficiently long to guarantee optimal adsorption of the calcium salt of the acid to be recovered; in practice, this time corresponds to a flow rate comprised between 0.2 volume and 5 volumes per volume of adsorbing resin, preferably at a flow rate of 0.5 volume to 1.5 volume per volume of resin.

The mixture was preferably a pH higher than 4.0 and a temperature comprised between 20° and 100° C. when it is contacted with the resin; preferably, this temperature is from 75° to 85° C.

The content of dry matter is a function of the solubility of the calcium salts involved; generally, it is comprised between 10 and 50%.

In a second phase, the resin previously saturated with the calcium salt of the acid to be recovered is eluted, by resorting to hot water, at a temperature in the vicinity of that of the medium in the preceding phase; generally, this temperature will hence be comprised between 75° and 85° C.

The amount of elution water used corresponds to a flow rate of 0.2 volume to 5 volumes per volume of resin, preferably to a flow rate of 0.5 volume to 1.5 volume per volume of resin.

The eluted fractions are collected in aliquot portions about of 20ths to 40ths of the volume of resin.

It is observed that, quite unexpectedly and surprisingly, the α-hydroxy- and α-amino-carboxylic acids in the form of their calcium salt, are not excluded from the macromolecular lattice of the cationic resin but are, on the contrary, strongly adsorbed. It follows that the first fractions eluted are enriched in oses, holosides or polyholosides, the latter fractions only being enriched in the calcium salt of the desired acid, the process according to the invention thus leading to a complete separation of said calcium salts, which, quite like the mixture of oses, holosides or polyholosides, containing them, are consequently recovered with high purity.

The process according to the invention which has just been described can be used by resorting to an installation comprising one or several chromatograph columns arranged in parallel, means adapted to supply this or these columns alternately with the mixture to be separated and by eluting them and means for collecting fractions.

Such an installation is shown in the single FIGURE.

This installation comprises a column 35 filled with resin R and supplied at its upper portion through a pipe 36 provided with a pump 37 and with a heating device 38. The pump 37 is connected through a pipe 39 to a vessel 42 filled with the mixture to be separated designated by A+B and by a pipe 40 to a container 43 filled with elution water. Through a pipe 41, the pump 37 is also connected to a container 44 which will be discussed below. Electrovalves 45, 46 and 47 are arranged respectively in the pipes 39, 40 and 41.

The column 35 is connected through a pipe 48 at its lower part to a container 49 and to a container 50, access to these two containers being made possible by the opening respectively of an electrovalve 51 and of an electrovalve 52. A third electrovalve 53 is provided in the pipe 48, the part 48a of this pipe situated downstream of the electrovalve 53 connecting the lower part of the column 35 to the above-mentioned container 44.

The operation of this installation is as follows.

In a first stage, the electrovalve 45 being open and the electrovalves 46 and 47 closed, the pump 37 leads mixture A+B through the pipe 36 into the column 35. From the moment when the column 35 can be considered as sufficiently loaded, the electrovalve 45 is closed, and after opening the electrovalve 46, the pump 37 leads the elution water to the column 35. By controlling suitably the opening and the closing respectively of the electrovalves 51, 52 and 53, taking into account the separation effect produced by the resin R contained in the column 35, the product A is led into the container 49, the product B into the container 50 and the low-concentrated waters (fraction comprised between the peaks respectively relating to the product A and to the product B) to the container 44. The use of these low-concentrated waters as eluting agent instead of elution water contained in the container 43 by opening the electrovalve 47 in place of the electrovalve 46 at the moment of elution, enables the volumes of water flowing in the installation to be reduced.

Below are applied, within the scope of a certain number of examples, the above-indicated general features of the process and of the installation according to the invention.

EXAMPLE 1

Separation of mixtures containing calcium gluconate, on the one hand, and glucose, galactose, fructose or mannose, on the other hand.

(a) Glucose—calcium gluconate separation 100 cm$^3$ of a solution containing 20 g of pure glucose and 10 g of calcium gluconate are proposed.

This solution is introduced with a flow rate of 2 cm$^3$/minute and at a temperature of 85° C. into a column of 90 cm height and 2 cm diameter, with a double thermostated jacket, filled with 400 ml of cationic resins of the sulphonated styrene-divinylbenzene type in the calcium form, of granulometry comprised between 0.2 and 0.4 mm and with a cross-linking ratio of 4% equipped at its outlet with a recording polarimeter of the BENDIX type and with a fraction collector capable of recovering fractions of 20 cm$^3$.

The elution is carried out by means of 500 cm$^3$ of water of temperature 80° C.

Each fraction is 20 cm$^3$.

For each fraction, there follows:

the determination of the soluble matter content expressed in percent of dry matter, determination of the angle of rotation L(P) obtained by means of a polarimeter and the determination of the specific rotatory power $(\alpha)_D$ which is obtained by the formula $$\alpha_D^{20} = L(P) \cdot M/V \cdot 1/l$$

in which M is the weight expressed in g, of the substance dissolved in the volume V in ml, and l the length of the polarimeter expressed in dm.

The results of these determinations are collected in Table I below:

TABLE I

| F | % of soluble materials | L(P) | α(D) | F | % of s soluble materials | L(P) | α(D) |
|---|---|---|---|---|---|---|---|
| 1 | 0 | — | — | 14 | 2.00 | +0.01 | +48.00 |
| 2 | 0 | — | — | 15 | 3.00 | +0.01 | +16.00 |
| 3 | 0 | — | — | 16 | 4.50 | +0.015 | +8.50 |
| 4 | 0 | — | — | 17 | 5.00 | +0.02 | +7.20 |
| 5 | 0 | — | — | 18 | 5.00 | +0.02 | +7.20 |
| 6 | 0 | — | — | 19 | 4.50 | +0.015 | +7.00 |
| 7 | 0 | — | — | 20 | 4.00 | +0.10 | +7.20 |
| 8 | 5.00 | +0.15 | +55.20 | 21 | 3.50 | +0.10 | +7.20 |
| 9 | 10.00 | +0.20 | +54.70 | 22 | 3.00 | +0.10 | +6.80 |
| 10 | 12.50 | +0.22 | +54.50 | 23 | 2.50 | +0.10 | +7.00 |
| 11 | 14.00 | +0.23 | +54.90 | 24 | 2.00 | +0.05 | +7.00 |
| 12 | 14.50 | +0.24 | +54.60 | 25 | 1.50 | +0.05 | |
| 13 | 10.60 | +0.06 | +53.20 | 26 | 0.05 | +0.05 | |

Figure 1:
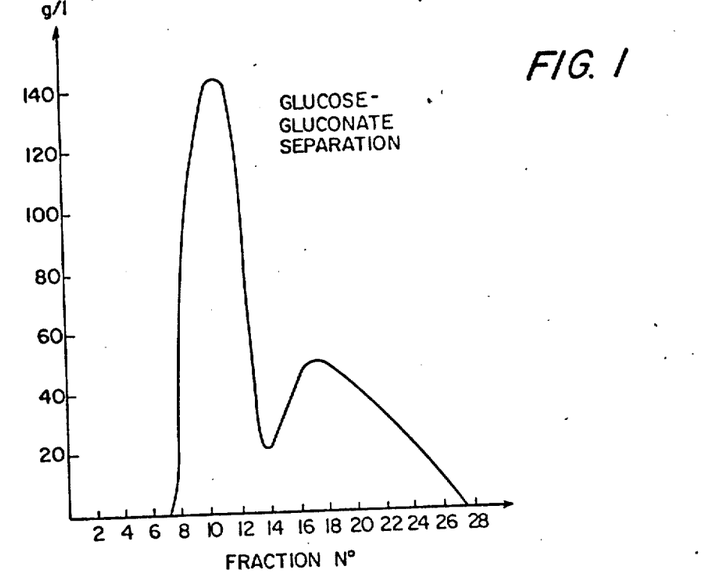

FIG. 1 shows the variation in the content of soluble material expressed in g/l as a function of the successive fractions collected.

This graph enables the successive outflow of the glucose and then that of the gluconate to be manifested (respectively fractions 8–14 and 14–27).

(b) Galactose—calcium gluconate separation

From pure crystalline lactose, after hydrolysis with sulphuric acid and precipitation of the calcium sulphate, biological oxidation of the glucose—galactose mixture obtained is carried out.

With 350 g/l in a medium supplemented with 10 g/l of corn steep liquor and 50 g/l of CaCO$_3$, by culturing a strain of Acetobacter suboxydans, the specific oxidation of the glucose contained in this stoechiometric mixture of glucose and galactose was achieved.

After purification by centrifugation, complete neutralization of the gluconic acid formed and recovery of a part of the calcium gluconate by crystallization, crystallization mother liquors were recovered containing 197 g/l of reducing sugars constituted essentially of galactose and 102 g/l of gluconic acid in the form of its calcium salt.

100 cm$^3$ of these mother liquors were treated by means of the equipment described in Example (a) and the same determinations were carried out.

Figure 2:
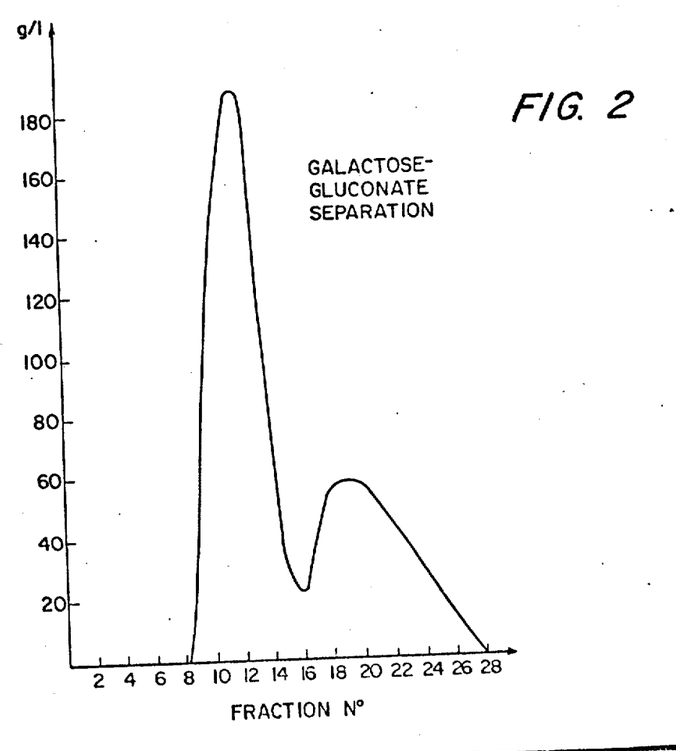

In FIG. 2 showing the content in g/l of the eluted fractions as a function of the fraction number, it is possible to check the outflow in two very distinct peaks: galactose at the first (fractions 8 to 15) and calcium gluconate at the second time (fractions 16 to 28).

(c) Fructose—calcium gluconate separation

From pure crystalline saccharose and after enzymatic hydrolysis with invertase, specific biological oxidation of the glucose and glucose—fructose mixture obtained was carried out; to do this, a strain of Acetobacter suboxydans was cultured on 350 g/l of glucids, in a culture medium supplemented with 7 g/l of Fould-Springer yeast extract and 50 g/l of CaCO$_3$.

After 48 hours of culture and by observing the variation in the measurement of dissolved oxygen, it was possible to oxidize the dextrose to 98% without oxidizing the fructose present in the culture must (culture medium).

After purification and recovery of a part of the calcium glucose by simple crystallization from the culture must completely neutralized with lime, the crystallization mother liquors were recovered which contained 204 g/l of reducing sugars essentially constituted by fructose and 98 g/l of gluconic acid in the form of its calcium salt.

On the column described in Example 1 (a), 100 cm³ of the thus-prepared mother liquors were treated. The elution was carried out with 550 cm³ of hot water at 80° C.

Certain of the determinations mentioned in Example 1 (a) were carried out and the results were combined in Table II.

TABLE II

| Fraction No. | Matter in g/liter |
|---|---|
| 1 | — |
| 2 | — |
| 3 | — |
| 4 | — |
| 5 | — |
| 6 | — |
| 7 | — |
| 8 | 22.5 |
| 9 | 85 |
| 10 | 121 |
| 11 | 150 |
| 12 | 195 |
| 13 | 145 |
| 14 | 50 |
| 15 | 25 |
| 16 | 30 |
| 17 | 42.5 |
| 18 | 55 |
| 19 | 51 |
| 20 | 45 |
| 21 | 35 |
| 22 | 24 |
| 23 | 15 |
| 24 | 7.5 |

Figure 3:
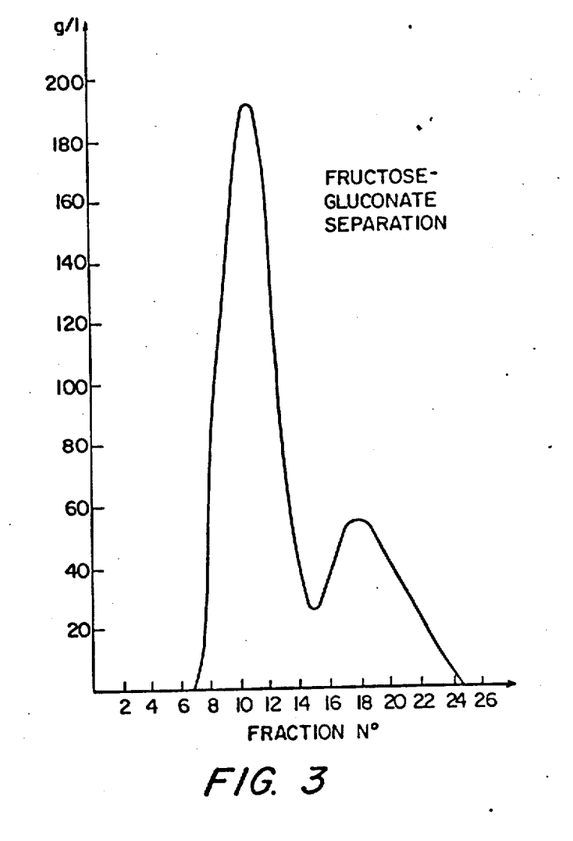

The FIG. 3 was drawn showing the content in g/l of the eluted fractions as a function of the fraction number.

This graph enables the outflow to be observed in two very distinct peaks: fructose in the first place (fractions 8 to 14) and calcium gluconate secondly (fractions 15 to 25).

Fractions 8 to 14 were brought together, demineralized with ion exchange resins, evaporated to 94% of matter and supplemented with a volume of ethanol.

Abundant crystallization of pure levulose was obtained: $\alpha D = -92°$.

From fractions 16 to 24 evaporated to 24% of dry matter and 70° C., abundant crystallization of calcium gluconate was obtained.

Another fructose—calcium gluconate separation experiment was carried out as follows.

From sugar and beetroot molasses, after inversion with sulphuric acid and neutralization with lime, biological oxidation of the dextrose-fructose mixture obtained was carried out by a semi-continuous process. The impurities contained in the molasses caused, for a concentration of 350 g/l, a much too considerable latent phase.

There was therefore, to a culture medium containing 7 g/l of Fould-Springer yeast and 50 g/l of $CaCO_3$, supplemented the equivalent of 100 g/l of glucide derived from molasses.

After 24 hours of culture and by means of the indications provided by the measurement of dissolved oxygen in the liquid phase, it was possible to add semicontinuously, hydrolyzed molasses up to a total content of 300 g/l.

This solution contained 140 g/l of reducing sugars essentially levulose and 160 g/l of calcium gluconate.

After centrifugation of the broth previously neutralized with lime, 8 liters of the broth were run into a column of 40 l filled with resin of the CA 9 220 type. After elution by means of 70 liters of water at 80° C., fractions of 2.5 l were recovered.

A considerable removal of color was observed at the head of the column and a separation in two waves: one containing levulose (fractions 10 to 14) and the second, calcium gluconate (fractions 15 to 25).

(d) Mannose—calcium gluconate separation

After isomerization at 120° C. and in the presence of 1 o/oo of ammonium molybdate of a solution of pure dextrose, a dextrose-mannose mixture was obtained with 36% of mannose and 64% of dextrose.

This mixture was oxidized specifically as previously described by resorting to an Acetobacter suboxydans strain.

After oxidation, purification and a first crystallization of the calcium gluconate, 100 cm³ of the solution of mother liquore were run onto a column of the type used in the preceding examples.

Figure 4:
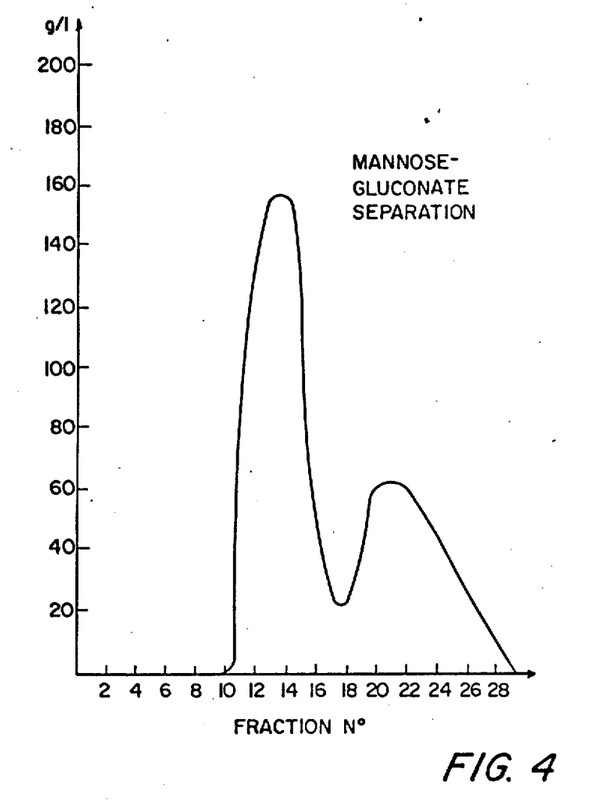

Repertorised determinations as in Example 1 (a) followed and the results were plotted (number of g/l as a function of the fraction number) on the FIG. 4.

From this Graph, it is clear that fractions 10 to 16 contain mannose; they were brought together, evaporated to 90% of matter and supplemented with a volume of methanol.

Abundant crystallization of pure mannose was obtained.

The fractions 18 to 28 contain calcium gluconate.

(e) Separation of calcium gluconate from a mixture of oses, holosides and polyholosides Production of calcium gluconate or of gluconodeltalactone from the byproducts of dextrose manufacture.

Production of pure dextrose can be carried out by hydrolysis of the $\alpha(1-4)$ bonds of the glucose units of starch by the consecutive action of $\alpha$-amylase and amylo-glucosidase: under normal industrial conditions (400 g/l of matter) hydrolysis to 94% is obtained.

The solution titrates 94% of real dextrose, the balance being constituted by di- and polyholosides which have escaped enzymatic action.

After purification and crystallization, 80% of the matter is recovered in the form of dextrose monohydrate.

The byproduct constituted by a hydrol of the second crop titrates at about 70 to 75% of pure glucose and 25 to 30% of a mixture of di- and polyholosides.

In a fermentor these crystallization mother liquors were placed in the proportion of 300 g/l in the presence of $CaCO_3$ and Corn Steep liquid in the proportion of 10 g/l.

At the end of fermentation, after 48 hours of biological oxidation by means of an Acetobacter suboxydans strain and after raising the dissolved oxygen level, the solution contained 240 g/l of calcium gluconate, the residual reducing sugar being constituted by maltose-isomaltose and many other polyholosides.

After centrifugation and filtration, an abundant crystallization of the calcium gluconate was obtained.

The mother liquors obtained contained a large amount of calcium gluconate whose recovery appeared impossible as a result of the presence of the abovementioned impurities.

15 liters of these mother liquors at 160 g/l of dry matter were run onto 40 liters of cationic resins with a cross-linking ratio of 4%, constituted by resins of the trademark LEWATIT CA 9 220, the flow rate being 400 cm³/min., the temperature 90° C.; elution was carried out, by means of 70 l of distilled water at a temperature of 90° C. The solution was recovered in fractions of 2.5 liters.

The determinations as in Example 1 (a) were carried out and the results are combined in Table III.

TABLE III

| F | % of soluble matter | L(P) | α(D) | F | % of soluble matter | L(P) | α(D) |
|---|---|---|---|---|---|---|---|
| 1 | 0 | — | — | 13 | 2.50 | −0.25 | −4.80 |
| 2 | 0 | — | — | 14 | 2.00 | −0.65 | −15.60 |
| 3 | 0 | — | — | 15 | 1.50 | −0.17 | −5.44 |
| 4 | 0 | — | — | 16 | 2.00 | +0.27 | +6.48 |
| 5 | 0 | — | — | 17 | 5.00 | +0.80 | +7.68 |
| 6 | 0 | — | — | 18 | 10.50 | +0.95 | +4.33 |
| 7 | 0 | — | — | 19 | 10.00 | +1.05 | +5.04 |
| 8 | 2.50 | +3.70 | +88.80 | 20 | 8.50 | +1.25 | +7.06 |
| 9 | 4.50 | +5.70 | +68.40 | 21 | 7.00 | +1.05 | +7.20 |
| 10 | 5.50 | +5.37 | +51.56 | 22 | 5.00 | +0.80 | +7.68 |
| 11 | 5.50 | +6.25 | +55.00 | 23 | 3.50 | +0.47 | +6.47 |
| 12 | 4.50 | +3.17 | +33.82 | 24 | 2.50 | +0.35 | +6.76 |

The fractions 8 to 15 contain polyholosides and the fractions 16 to 24 contain calcium gluconate.

EXAMPLE 2

Separation of calcium xylonate from a mixture of oses

From a hydrolysate of corn cobs and after purification, pure xylose was crystallized.

The mother liquors after crystallization of the pure xylose contain a mixture of pentoses and hexoses, principally constituted by xylose-arabinose-galactose and glucose.

By biochemical oxidation with a strain of Acetobacter suboxydans, it was possible to oxidise the xylose and the glucose specifically.

After oxidation and purification, 40 cm³ of a solution with 250 g/l of dry matter were sent at a flow rate of 2 cm³/minute at 80° C. onto the column described in Example 1 (a) filled with CA 9 220 resin. The effluent was recovered by fractions of 20 cm³.

For each fraction the content of dry matter (g/l) was determined and these results are combined in Table IV below.

TABLE IV

| Fraction No. | Dry matter in g/liter | Fraction No. | Dry matter in g/liter |
|---|---|---|---|
| 1 | — | 16 | 20 |
| 2 | — | 17 | 25 |
| 3 | — | 18 | 25 |
| 4 | — | 19 | 20 |
| 5 | — | 20 | 28 |
| 6 | — | 21 | 34 |
| 7 | — | 22 | 40 |
| 8 | 8 | 23 | 42 |
| 9 | 12 | 24 | 44 |
| 10 | 19 | 25 | 40 |
| 11 | 19 | 26 | 33 |
| 12 | 24 | 27 | 26 |
| 13 | 30 | 28 | 20 |
| 14 | 37 | 29 | 12 |
| 15 | 35 | 30 | 8 |

Figure 5:
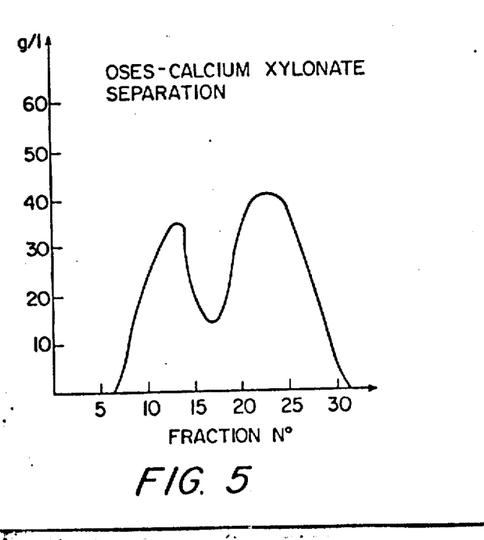

The data from this table were plotted in FIG. 5.

From this Graph, it is possible to conclude that fractions 7 to 17 are constituted by non-oxidized oses and fractions 18 to 32 by xylonate and calcium gluconate.

EXAMPLE 3

Purification of calcium lactate

The production of lactic acid or of calcium lactate by anaerobic fermentation is an old and well-known process.

This anaerobic fermentation, compared with the production of citric acid for example, consumes little energy, it produces in addition 100 to 150 g of lactic acid per liter of broth in two to three days of fermentation.

This fermentation, on the other hand, provides high yields of lactic acid, of about 90%, even from cheap glucid sources (molasses-hydrols constituting byproducts of dextrose production).

It presents unfortunately a serious drawback; it is very demanding of additional nutrient materials, organic nitrogen materials, oligo-elements, soluble vitamins and the like. The high percentage of these soluble materials renders the refining process of the calcium lactate and especially of the lactic acid difficult, notably to produce food grade calcium lactate and lactic acid.

The crystallization of the calcium lactate enables purification of the product, but gives incomplete yields, and a high percentage (30 to 50%) of the lactate produced remains in the last crystallization mother liquors. Moreover, in the course of the crystallization, colloid precipitation phenomena occur which lead to the production of the calcium lactate having turbidity in solution not in accordance with the CODEX or with food standards.

Many other purification processes for lactic acid regenerated from broth are known in addition to crystallization of the calcium lactate.

The use of these processes presents numerous drawbacks and still does not enable the production of products of good food quality. Solvent or byproduct residues may remain in the lactic acid.

For all these reasons, it has been thought that the purification should be carried out without the use of solvent.

In a tube of 90 cm height, 2 cm diameter with a double thermostated jacket and equipped with a fraction collector, the mixture dextrose-calcium lactate (10% solution of dextrose and lactate) was treated to study the influence of the flow rate, of the temperature and of the amount of product to be separated. To do this, the effluent was analysed in series on a continuous automatic Bendix polarimeter and on a UV cell for the measurement of the soluble proteins.

The resin used was that of the CA 9 220 type, the temperature being 80° C., that of the elution water 80° C. and the flow rate studied 200, 250, 400, and 600 cm³/hour.

There was observed for each of these flow rates a complete separation of the dextrose and of the calcium lactate, the dextrose emerging in first position, the lactate in second position completely separated.

Identical tests were then carried out at 40°, 60°, 80° and 90° C. and at a flow rate of 200 cm³/hour.

No substantial difference was observed between the various separations.

From the abovesaid solution, separations of 50, 100, 150, 200 and 225 cm³ of solution were carried out.

In each case, it was possible to recover the dextrose, on the one hand, and calcium lactate on the other hand, with the highest possible dry matter.

There are hence no critical values regarding the three abovesaid parameters.

The temperature can be raised without difficulty up to 80°–90° C. At this temperature, separation flow rates higher than or equal to 600 cm³/hour can be envisaged.

Considerable amounts of mixture can be separated; in the present case 200 cm³ of the mixture represent 50% of the volume of the material.

(a) Separation from a broth

Broths derived from the fermentation of dextrose were treated, namely the hydrol H1 byproduct of the first crystallization of the dextrose, then the hydrol H2 byproduct of the second crystallization of the dextrose.

In all cases, the fermentation had been carried out in less than 72 hours by Lactobacillus Delbrucki. The total disappearance of reducing sugars in less than 72 hours and the formation of 110–120 g/l of lactic acid at the end of the fermentation, were noted. The purification was carried out by a treatment with lime at pH 9.0 and at a temperature of 90° C.; it was terminated by filtration.

The filtered culture must normally has 16% of dry matter.

In the case of the hydrol H1, the separation was carried out to 25% of dry matter after evaporation.

In the case of the hydrol H2, the separation was carried out to 18% of dry matter.

The equipment used was that described above.

The conditions of the experiment relating to the treatment of 100 cm³ of solution were:

| temperature: | 80° C. |
|---|---|
| flow rate: | 200 cm³/hour |
| elution: | water at 80° C. |

The separation curves show the outflow of the calcium lactate into the 17th fraction.

The preceding fractions are very colored, they precipitate with alcohol for a dilution with 500% of alcohol (presence of proteins). They are cloudy in solution and loaded with inorganic matter.

From the combined lactate fractions, the crystallization of the calcium lactate was carried out.

The group of these fractions with 60 g/l of lactate was adjusted to a pH of 5.5 with a little pure lactic acid. The solution was decolorized on a PITTSBURGH charcoal column, evaporated to 150 g/l, filtered on a COFRAM type bacteriological filter.

After 48 hours of crystallization up to ordinary temperature, draining and drying of the product, 75% of the total calcium lactate was recovered in the pentahydrate form.

The calcium lactate was in accordance in all respects with the pharmaceutical qualities described in the CODEX.

By way of comparison, it is indicated that the crystallization carried out directly from culture musts in addition to the impossibility of decolorizing them, leads to a lactate which is cloudy (turbid) in 10% solution and colored.

(b) Separation from molasses.

Pure calcium lactate was recovered from a broth obtained by molasses fermentation.

In the case of molasses as a raw material, the purification of calcium lactate and of lactic acid is still more laborious; the molasses being the residue of dextrose crystallization, it contains a considerable percentage of sugars in the form of various inorganic substances and in the form of organic impurities.

This group of these impurities always contaminates the calcium lactate and lactic acid obtained by fermentation of molasses. This is the reason why it is observed that numerous producers of lactic acid use pure sugar for the production of food or pharmaceutical qualities of lactic acid or of calcium lactate.

The lactic fermentation was carried out (Lactobacillus Delbruckis strain) on molasses (120 g/l of total reducing sugars). In less than 48 hours, at a temperature of 47° C., 117 g/l of lactic acid were obtained.

After purification by treatment with lime and filtration, purifications by ion exchange resins were carried out by treating 100 cm³ containing 180 g/l of matter, then 100 cm³ containing 300 g/l of material obtained by evaporation.

The equipment used was that described above and the conditions were as follows:

| temperature: | 80° C. |
|---|---|
| dry matter: | 18° Brix and 30° Brix |
| flow rate: | 200 cm³/hour |
| elution: | water at 80° C. |

Analysis of the fractions collected show an outflow in two waves, the first containing colloides, proteins, mineral salts, and traces of residual glucids, and the second, the highly decolorized soluble calcium lactate.

The fractions of lactate were combined, decolorized on activated charcoal, and evaporated to 150 g/l.

Crystallized for 48 hours and dried, they gave more than 70% of pure lactate pentahydrate, of pharmaceutical quality.

Tests carried out from the broths have given cloudy (turbid) technical lactates in 10% solution and colored.

(c) Separation from a must (medium) prepared on the basis of hydrol H2

After fermentation in a fermentor of 300 liters from a hydrol H2 with 120 g/l of glucids, the broth was filtered, previously coagulated with lime, at a temperature of 90° C.

Analysis of the broth after filtration gives the results:

| Bx | 16% of matter |
|---|---|
| Acidity | 108 g/l |
| Reducing sugars | 0.12 g/l |
| Reducing sugars after hydrolysis | 0.16 g/l |
| L-lactic acid | 59 g/l |
| D-lactic acid | 44 g/l |
| Total | 103 g/l |

At a flow rate of 32 liters/hour (1 volume/hour) at a temperature of 80° C., on to a column 2 meters high, of diameter 25 cm, lined with 40 ml of type CA 9 220 resin, was run 8 liters of filtered broth with 15.5% of dry matter followed by 20 liters of distilled water whose temperature was 80° C.

The effluent was separated in two fractions: 18 liters of impurities containing colloids, colored substances, proteins and other impurities and 15 to 17 liters of purified calcium lactate. The concentration of lactate was 55 g/l.

This lactate thus purified was evaporated to 250 g/l.

Precipitation of the calcium was effected with sulphuric acid.

The calcium sulphate was filtered off, the solution of lactic acid was purified by passing over a cationic resin to remove the soluble calcium, then over an anionic resin to remove the soluble sulphate.

After decoloration on granulated activated charcoal, placed in columns 2 meters high, the clear and decolorized solution was evaporated to 80% of dry matter.

This lactic acid solution which was in the form of a syrupy liquid, almost odorless, very slightly yellowish, corresponds to the following analysis:

|  | Lactid acid obtained | F.C.C. Standards* |
|---|---|---|
| Richness | 99.5 | 95–105 |
| Arsenic | 0 | 3 ppm |
| Cl | 0 | 0.2% |
| Citric | conforming | |
| Oxalic | with F.C.C. | see tests |
| Phosphoric | standards | |
| Tartaric | | |
| Heavy metals | conforming with F.C.C. standards | |
| Iron | 0.2 | 10 ppm |
| Sugars | negative | see tests |
| Sulphate | negative | 0.25% |
| Calcium | negative | 2 |
| Coloration | 99% transmittance at 540 | |
| Specific gravity | 1.92 | |

*F.C.C. = Food Chemical Codex, that is to say according to international standards ruling the quality of food products.

This acid is in all respects in accordance with FOOD CHEMICAL CODEX food quality (standard defined above).

From this same solution of lactate at 55 g/l, after adjustment of the pH to 5.5, evaporation to 150 g/l, decoloration on a column of charcoal, filtration on a bacteriolic filter, crystallization, draining and drying on a fluidized bed, a calcium lactate was obtained which corresponds to the following analysis:

| Identity | conforming with French Pharmacopea |
|---|---|
| Appearance | fine powder |
| Color | white |
| Odour | odourless |
| 5% solution | clear |
| Color | none |
| Lose of weight at 105° C. | 27.5% |
| Titer in % dry | 99.3% |
| on 5 H$_2$O | 101.7% |
| Heavy metals | |
| Pb | 2 ppm |
| Iron | 8 ppm |
| Ba | 0 |
| Mg | 290 mg/kg |
| Cl | 24 mg/kg |
| SO$_4$ | 0 |
| Reducing sugars | 0 |
| Volatile fatty acids | 0 |

This lactate is in accordance with pharmaceutical standards.

EXAMPLE 4

Separation of glutamic acid and glucose

The α-amino acids in the form of their calcium salts may be separated from the oses or from polyholosides.

The separation is carried out on the same equipment as that described in Example 1 (a) and under the same conditions, of a mixture of calcium glutamate and glucose.

To do this a flow rate of 200 ml/hour was used, 20 ml of said mixture containing 2 g of glutamic acid neutralized by CaO and 2 g of glucose.

The operating temperature was 80° C. The effluent was recovered in the form of fractions of 20 ml after elution by means of water at 80° C. The content of dry matter was determined for each of the 22 fractions collected.

Figure 6:
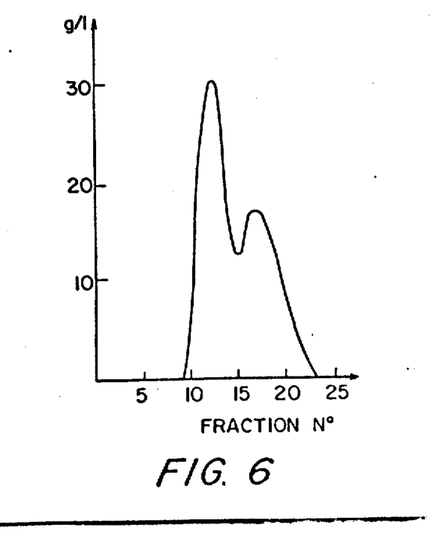

The values are combined in Table V below and the corresponding FIG. 6.

TABLE V

| Fraction No. | Dry Matter g/l |
|---|---|
| 1 | — |
| 2 | — |
| 3 | — |
| 4 | — |
| 5 | — |
| 6 | — |
| 7 | — |
| 8 | — |
| 9 | — |
| 10 | 0.5 |
| 11 | 1.8 |
| 12 | 2.7 |
| 13 | 3.0 |
| 14 | 1.7 |
| 15 | 1.2 |
| 16 | 1.4 |
| 17 | 1.7 |
| 18 | 1.6 |
| 19 | 1.2 |
| 20 | 0.8 |
| 21 | 0.3 |
| 22 | 0 |

The outflow of the glucose occurs in fractions 9 to 15 and that of the glutamate in fractions 15–22.

EXAMPLE 5

Separation of calcium aspartate and glucose

In the same way as in Example 4, the separation of a mixture with 200 g/l of glucose and 200 g/l of calcium aspartate was carried out.

The amount subjected to chromatography was also 20 ml at a flow rate of 200 ml/hour and at 80° C. The elution was effected with water at 8° C.

The fractions were collected in the same manner as indicated above and were analysed on the basis of their dry matter content.

Figure 7:
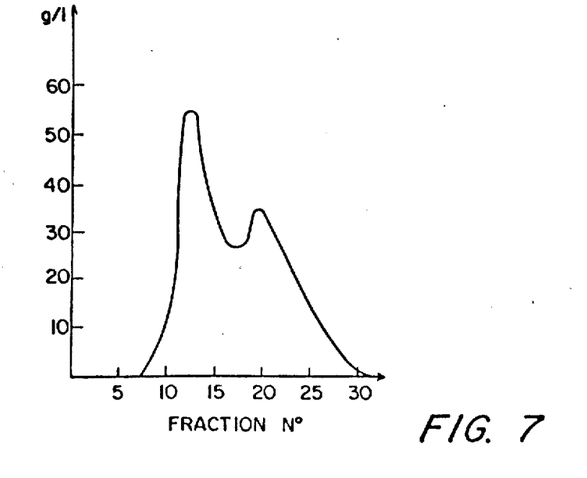

Table VI and FIG. 7 illustrate the results obtained.

TABLE VI

| Fraction No. | Dry Matter g/l |
| --- | --- |
| 1 | — |
| 2 | — |
| 3 | — |
| 4 | — |
| 5 | — |
| 6 | — |
| 7 | — |
| 8 | 0.2 |
| 9 | 0.5 |
| 10 | 1.0 |
| 11 | 2.2 |
| 12 | 3.8 |
| 13 | 5.4 |
| 14 | 5.4 |
| 15 | 4.0 |
| 16 | 2.8 |
| 17 | 2.6 |
| 18 | 2.6 |
| 19 | 3.2 |
| 20 | 3.4 |
| 21 | 3.2 |
| 22 | 2.8 |
| 23 | 2.3 |
| 24 | 1.8 |
| 25 | 1.4 |
| 26 | 1.0 |
| 27 | 0.7 |
| 28 | 0.5 |
| 29 | 0.2 |
| 30 | 0 |

The curve representing the variation of the content of dry matter as a function of the fraction number is shown in FIG. 7.

Fractions 8–16 contain glucose and fractions 18–29 calcium aspartate.

On examining the whole of the foregoing results, it is observed that, by means of the process according to the invention, the separation of α-hydroxy- and α-aminocarboxylic acids in the form of their calcium salts from sugary media containing them is quantitative, said calcium salts being recovered with a degree of purity of more than 90%.

As is self-evident and as emerges already from the foregoing, the invention is in no way limited to those of its types of application and embodiments which have been more especially envisaged; it encompasses, on the contrary, all modifications.

We claim:

1. Process for recovering α-hydroxy- and α-aminocarboxylic acids in the form of their calcium salts from sugary media containing them, wherein:
   in the first step, said sugary media containing an α-hydroxy- or α-amino-carboxylic acid in the form of its calcium salt is contacted with a cationic resin in the calcium form for a sufficient time to achieve an optimal adsorption of said calcium salt and then,
   in a second step, the previously saturated resin is eluted by water to provide first fractions enriched in sugar and then latter fractions enriched essentially in an α-hydroxy- or α-aminocarboxylic acid in the form of its calcium salt, recovering thus the said acid in the form of its calcium salt.

2. Process according to claim 1, wherein the time of contact between the mixture to be treated and the resin corresponds to a flow rate comprised between 0.2 volume and 5 volumes per volume of adsorbing resin.

3. Process according to claim 2, wherein the time of contact corresponds to a flow rate comprised between 0.5 volume to 1.5 volume per volume of resin.

4. Process according to claim 1, wherein both the mixtures subjected to treatment and the elution water are used at a temperature comprised between 20° and 100° C.

5. Process according to claim 4, wherein the temperature is comprised between 75° and 85° C.

6. Process according to claim 1, wherein the cationic resin if of the sulphonated styrene-divinyl-benzene type in its calcium form of a grain size range comprised between 0.1 and 1 mm, the cross-linking ratio of said resin being comprised between 2 and 10%.

7. Process according to claim 6, wherein the grain size range of the cationic resin is comprised between 0.2 and 0.6 mm.

8. Process according to claim 6, wherein the cross-linking ratio of the cationic resin is comprised between 3 and 5%.

9. Process according to claim 1, wherein it is applied to the recovery of calcium gluconate from sugary media containing it and which have been used for its preparation by specific biochemical oxidation.

10. Process according to claim 1, wherein it is applied to the recovery of calcium xylonate from sugary media containing it and which have been used for its preparation by specific biochemical oxidation.

11. Process according to claim 1, wherein it is applied to the recovery of calcium lactate from sugary media containing it and which have been used for its preparation by specific biochemical oxidation.

12. Process according to claim 1, wherein it is applied to the recovery of calcium glutamate from sugary manufacturing media containing it.

13. Process according to claim 1, wherein it is applied to the recovery of calcium aspartate from sugary media containing it.

* * * * *

UNITED STATES PATENT AND TRADEMARK OFFICE
CERTIFICATE OF CORRECTION

PATENT NO. : 4,288,619            Page 1 of 4

DATED : September 8, 1981

INVENTOR(S) : Francis Devos et al.

It is certified that error appears in the above—identified patent and that said Letters Patent is hereby corrected as shown below:

Figures 1 through 7 should appear as part of Letters Patent as per the attached sheets.

Signed and Sealed this

Second Day of March 1982

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,288,619
DATED : September 8, 1981
INVENTOR(S) : Francis DEVOS et al It is certified that error appears in the above-identified patent and that said Letters Patent are hereby corrected as shown below:

IN THE DRAWINGS

Label the schematic figure of the installation

--Fig. 8--.

Col. 3, line 1, after "FIGURE" insert --8--.

Signed and Sealed this

Seventeenth Day of August 1982

[SEAL]

Attest:

GERALD J. MOSSINGHOFF

Attesting Officer     Commissioner of Patents and Trademarks